US00PP10178P

United States Patent [19]

Donnelly et al.

[11] Patent Number: Plant 10,178

[45] Date of Patent: Jan. 6, 1998

[54] *CUPRESSUS GLABRA* PLANT NAMED 'LIMELIGHT'

[76] Inventors: Ruth Donnelly; Peter Donnelly, both of RMB 5510 Coachwood, Matcham, NSW 2250, Australia

[21] Appl. No.: 647,398

[22] Filed: May 8, 1996

[51] Int. Cl.[6] ..... A01H 5/00

[52] U.S. Cl. ..... Plt./50.1

[58] Field of Search ..... Plt./50.1, 50.2, Plt./50.3

[56] References Cited

PUBLICATIONS (UPOVROM Listing) AU PBR 91/051 for 'Limelight' published Jun. 18, 1992.

(UPOVROM Listing) NZ PBR TRMOZO for 'Limelight' published Jan. 14, 1996.

*Primary Examiner*—James R. Feyrer

*Attorney, Agent, or Firm*—Christie, Parker & Hale, LLP

[57] ABSTRACT

A new *Cupressus glabra* plant having an erect and slender growth habit and capable of year-round light yellow to lime-green color foliage.

1 Drawing Sheet

BACKGROUND OF THE INVENTION

The present invention relates to a new and distinct variety of *Cupressus glabra* which was discovered as a seedling in a controlled planting of *Cupressus glabra* plants. The varietal denomination of this new variety is 'Limelight'.

SUMMARY OF THE INVENTION

The new variety possesses a combination of characteristics which distinguish from its parent and all other varieties of which I am aware. Among these characteristics are foliage of a light yellow to lime-green color foliage, compact growth habit, acutely angled and slightly arching (concave) branches which result in an erect and slender growth habit, branchlets with short internode lengths and the capability of providing light yellow to lime-green foliage all year.

Asexual reproduction by vegetative cuttings of the new variety as performed in New South Wales, Australia, shows that the foregoing and other distinguishing characteristics come true to form and are established and transmitted through succeeding propagations.

BRIEF DESCRIPTION OF ILLUSTRATIONS

The accompanying illustrations show typical specimens of the vegetative growth of the new variety identified in the illustrations as *C. glabra* 'Limelight' and a comparison with other varieties, depicted in color as nearly true as it is reasonably possible to make the same in a color illustration of this character.

The top photograph depicts, in close view, the terminal portions of stems of a typical specimen of *Cupressus glabra* on the left; of the new plant 'Limelight' in the middle; and of the plant 'Aurea' on the right. This photograph shows the coloration, character and density of the needles of each variety, and the newly formed stem colors and thicknesses.

In the bottom photograph, whole specimens of comparison plants are shown, with a specimen of 'Aurea' positioned on the left; a specimen of 'Limelight' in the middle, and a typical specimen of *Cupressus glabra* positioned on the right. In this photograph, the differences in habit and coloration of the comparison plants can be seen.

COMPARISON WITH OTHER VARIETIES

The accompanying illustrations show *Cupressus glabra*, *Cupressus glabra* 'Aurea', and *Cupressus glabra* 'Hinlime'. As can be seen, 'Hinlime' differs in branch coloring of upper and lower branchlet surfaces compared to both 'Aurea' and the common form of glabra.

'Hinlime' has a narrow conical shape and a compact growth habit due to its vertical branching characteristics and short inter-branchlet spacing. In this respect, 'Hinlime' resembles the more narrow forms of *Cupressus glabra*, and is distinguished from *Cupressus glabra* 'Aurea', which has a more open, sideways branching habit resulting from a larger inter-branchlet interval and flat to convex branching angle to the main stem.

All characteristics described in Table 1 are from the comparative growing trials conducted at Matcham, New South Wales, Australia, from 20 plants of each variety grown outdoors in 20 cm diameter pots. The potting mix consisted of sand, pinebark and composted sawdust fertilized with a slow-release plant food. Measurements are from branchlets samples at random from each of the 20 plants in the trial.

TABLE 1

| | 'LIMELIGHT' | *C. glabra* 'AUREA | *C. glabra*, Common Form |
|---|---|---|---|
| Branchlet Upper Surface Summer Color | Near 8B | Near 151A | Near 189B |
| Branchlet Lower Surface Summer Color | Near 154B | Near 144A | Near 189B |
| Distance Between Branchlet | | | |
| Mean | 13.5 mm | 23.2 mm | 22.2 mm |
| Range | 3–30 | 10–55 | 5–50 |
| Std. Deviation | 5.46 | 11.13 | 12.32 |
| No. Measured | 113 | 97 | 103 |
| Angle of Branchlet to Main Stem | | | |
| Mean | 46.5° | 85° | 35° |
| Range | 15–75 | 25–130 | 10–70 |
| Std. Deviation | 13.75 | 26.55 | 15.23 |
| No. Measured | 71 | 46 | 79 |
| Stem Diameter-30 CM from Apex | | | |
| Mean | 4.6 mm | 4.1 mm | 3.8 mm |

TABLE 1-continued

| | 'LIMELIGHT' | *C. glabra* 'AUREA | *C. glabra*, Common Form |
|---|---|---|---|
| Range | 4–5.5 | 3.5–5 | 3–5 |
| Std. Deviation | 0.44 | 0.42 | 0.78 |
| No. Measured | 15 | 15 | 10 |
| Plant Width | | | |
| Mean | 36.7 mm | 53.4 mm | 28 mm |
| Range | 31–43 | 45–66 | 20–36 |
| Std. Deviation | 3.16 | 5.44 | 4.37 |
| No. Measured | 17 | 15 | 18 |

DETAILED DESCRIPTION OF THE NEW VARIETY

Origin: Seedling found in a controlled cultivated planting of *Cupressus glabra* plants.
Parentage: *Cupressus glabra.*
Classification: *Cupressus glabra* 'Limelight'.

The following is a detailed description of the new variety of the specimens grown in New South Wales, Australia. The colored terminology used is in accordance with The Royal Horticultural Society Colour Chart (R.H.S.C.C.), and refers to plate numbers in the aforementioned color chart. Phenotypic expression may vary depending on light, environmental, and cultural conditions.

Plant

1. Overall size and growth habit:
   A. *Size.*—The ultimate size is unknown. The original mother plant from which the initial cuttings were collected is now about 18' (5.5 m) tall with an approximate spread of about 4' (1.2 m); the speed of grown is slowing down.
   B. *Height.*—About 18'/5.5 m.
   C. *Width.*—About 4'/1.2 m.
   D. *Habit.*—Narrow, upright conical forms with a compact growth habit.
2. Foliage:
   A. *Arrangement.*—Scale-like, small, very densely arranged, overlapping, juvenile foliage — needle-form.
   B. *Branchlet.*—Not on an even plane, rather spreading in all direction, 4-sided, flattened.
   C. *Needles.*—Evergreen scales closely overlaping, scale-like, flattened to branchlet, and superposed in 4 rows, about one-sixteenth inch long, acutely pointed, yellow to lime-green.
3. Size:
   A. *Average leaf length.*—1/16"/1.5–2 mm.
   B. *Shape.*—Needles flattened to branchlet.
   C. *Texture.*—Fine.
4. Color:
   A. *Upper leaf surface.*—Near 8B.
   B. *Lower leaf surface.*—Near 154B.
5. Inflorescence:
   A. *Flowers.*—Monoecious, with male in small oblong cones, yellowish in color; female in a subglubose cone.
   B. *Form.*—Male; small oblong, stamens each with 2 pollen sacs.
   C. *Arrangement.*—Male flowers; small, oblong, stamens each with 2 pollen sacs. Female flowers; several, small decussate bracts, these with numerous seed chamber (ovules)at the base.
6. Reproductive system:
   A. *Fruit.*—Globose cone with 6 to 8 flat or slightly depressed scales, each contracted into a short mucro (point), 1 to ¼" wide, 1" long; scales are peltate.
   B. *Seed.*—4–5 mm long, blue pruinose.
7. Non-visual characteristics:
   A. *Fragrance.*—Medium; needles have very active resin glands.
   B. *Ease of propagation.*—Readily roots with no qualifications.
8. Hardiness:
   A. *USDA hardiness zone* 7A.—0° to 5° (°F.).

We claim:

1. A new and distinct variety of *Cupressus glabra* plant named 'Limelight', substantially as shown and described.

* * * * *

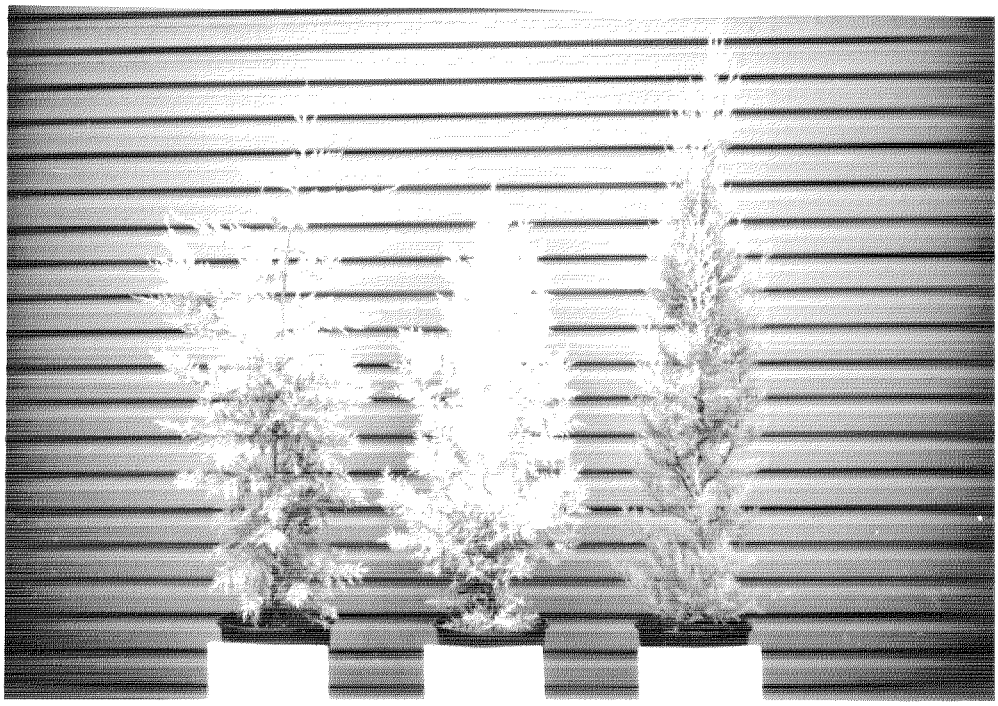

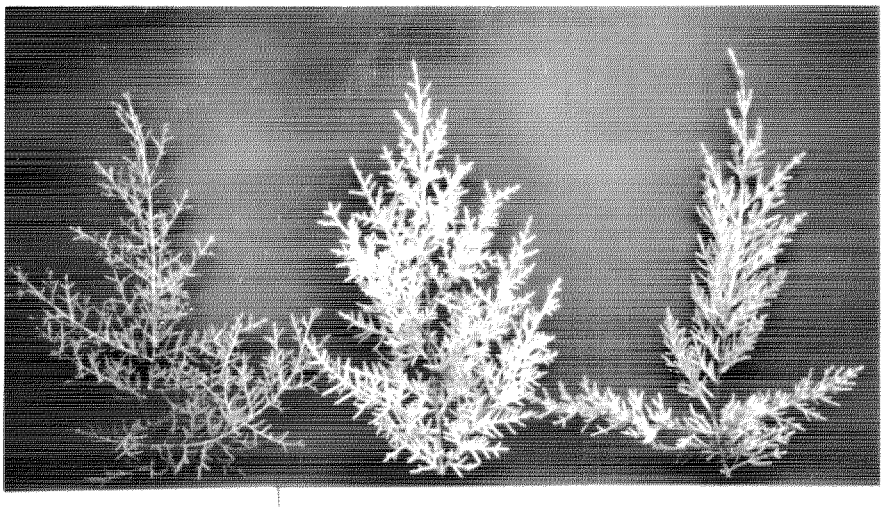
C glabra | C glabra L meigh+ | glabra Aurea